United States Patent [19]

Baldwin

[11] Patent Number: 5,066,797
[45] Date of Patent: Nov. 19, 1991

[54] PROCESS FOR PREPARING CEPHAM INTERMEDIATES

[75] Inventor: Jack E. Baldwin, Hinksey Hill, England

[73] Assignee: Lilly Industries Limited, Hampshire, England

[21] Appl. No.: 377,371

[22] Filed: Jul. 10, 1989

[30] Foreign Application Priority Data

Jul. 12, 1988 [GB] United Kingdom ............... 8816546

[51] Int. Cl.$^5$ .......................................... C07D 501/04
[52] U.S. Cl. ..................................... 540/215; 540/222; 540/221
[58] Field of Search ............... 540/215, 230, 221, 222

[56] References Cited

U.S. PATENT DOCUMENTS 4,558,123 12/1985 McShane ........................... 540/215
4,958,018 9/1990 Torii et al. ......................... 540/215

Primary Examiner—Nicholas S. Rizzo
Attorney, Agent, or Firm—William B. Scanlon; Leroy Whitaker

[57] ABSTRACT

There is described a process for producing exomethylene cepham intermediates useful in cephalosporin chemistry. The process comprises the preparation of a compound of the formula

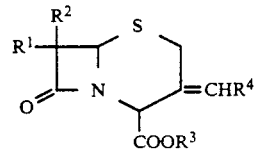

in which
$R^1$ is an amino group, a protected amino group, an acylamino group or a diacylamino group,
$R^2$ is hydrogen, $C_{1-4}$ alkoxy or $C_{1-4}$ alkylthio,
$R^3$ is hydrogen, a salt ion or an ester-forming group, and
$R^4$ is hydrogen or $C_{1-3}$ alkyl,
by reacting a compound of the formula

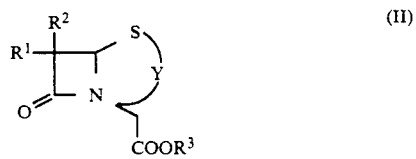
(II)

in which Y is a bridging group of the formula

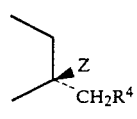

or

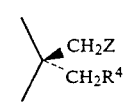

Z is chloro, bromo or iodo, and $R^1$, $R^2$, $R^3$ and $R^4$ have the above defined values, with a reagent providing cobalt I, under reducing conditions.

8 Claims, No Drawings

PROCESS FOR PREPARING CEPHAM INTERMEDIATES

This invention relates to a process for preparing exomethylene compounds useful as intermediates in the preparation of antibiotics.

Exomethylene derivatives of the cephalosporin nucleus are employed in the synthesis of antibiotic products. For example, Chauvette in U.S. Pat. No. 3,925,372 describes the production of the 3-chloro-cepham antibiotic known as cefaclor, by the ozonolysis of a 3-exomethylene cepham to 3-hydroxy-3-cepham, followed by halogenation. Other antibiotics can be prepared from the appropriate 3-exomethylene 1-oxide and 1,1-dioxide cephams.

The invention provides a process for preparing a compound of the formula

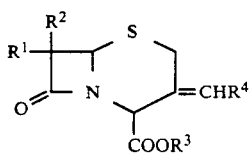  (I)

in which
$R^1$ is an amino group, a protected amino group, an acylamino group or a diacylamino group,
$R^2$ is hydrogen, $C_{1-4}$ alkoxy or $C_{1-4}$ alkylthio,
$R^3$ is hydrogen, a salt ion or an ester-forming group, and
$R^4$ is hydrogen or $C_{1-3}$ alkyl,
which comprises reacting a compound of the formula

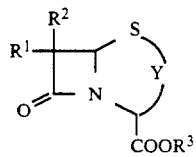  (II)

in which Y is a bridging group of the formula

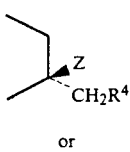

or

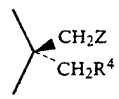

Z is chloro, bromo or iodo, and $R^1$, $R^2$, $R^3$ and $R^4$ have the above defined values, with a reagent providing cobalt I, under reducing conditions.

The process of the invention is readily and conveniently carried out and gives good yields of the desired product.

Because the process of the invention involves only the halo atom and neighbouring alkyl groups on the nucleus, the particular $R^1$ group in the above formula is not critical to the process. When $R^1$ is an acylamino group, the acyl residue can be chosen from numerous and varied acyl residues known in the cephalosporin and penicillin arts. Preferably the acyl residue is one which is not easily reducible so that alterations of the residue do not occur during the reaction. In particular when $R^1$ is an acylamino group, it can be:

an acylamino group of the formula $R^5CONH$— in which $R^5$ is hydrogen or $C_{1-4}$ alkyl optionally substituted by halogen, cyano or hydroxy;
a heteroarylacylamino or arylacylamino group of the formula

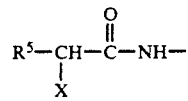

in which $R^5$ is thienyl, benzothienyl, furyl, benzofuryl, thiazolyl, oxazolyl, isoxazolyl, isothiazolyl, pyrazolyl, thiadiazolyl, oxadiazolyl, pyridyl, or these heterocyclic rings substituted by $C_{1-4}$ alkyl, amino, protected amino, or hydroxy; cyclohexadienyl, naphthyl, phenyl, or a substituted phenyl group represented by the formula

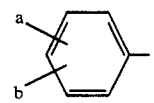

in which a and b, independently, are hydrogen, halogen, hydroxy, $C_{1-4}$ alkyl, $C_{1-4}$ alkoxy, amino, aminomethyl, methylsulphonylamino, hydroxymethyl, trifluoromethyl, carboxy, protected carboxy, carboxymethyl, or protected carboxymethyl;

X is hydrogen, hydroxy, $C_{1-4}$ alkanoyloxy, carboxy, protected carboxy, sulpho($-SO_3H$), amino, protected amino, or X is a substituted amino group represented by the formula

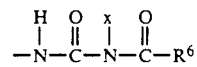

in which $R^6$ is furyl, thienyl, phenyl, halophenyl, nitrophenyl, styryl, halostyryl, nitrostyryl, or a group of the formula

in which $R^7$ is hydrogen, $C_{1-4}$ alkyl, benzyl, $C_{2-5}$ alkanoyl, or $C_{1-3}$ alkylsulphonyl, and x and y, when taken separately, are hydrogen or $C_{1-4}$ alkyl, and when taken together form a 5- or 6-membered ring represented by the formula

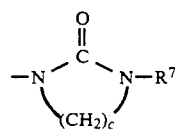

in which $R^7$ has the same meanings as defined above and c is 2 or 3; or

X is a substituted amino group of the formula

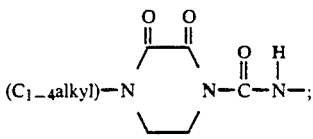

or

X is a benzamido group represented by the formula

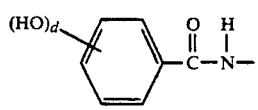

in which d is an integer of from 1 to 3; an acylamino group of the formula

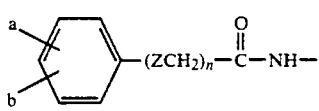

in which a and b have the same meanings as defined above, Z is O or S, and n is 0 or 1; or
an oximino-substituted acylamino group of the formula

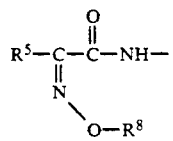

in which $R^5$ is as defined above, and $R^8$ is hydrogen, $C_{1-4}$ alkyl, or a carboxy-substituted alkyl or cycloalkyl group of the formula

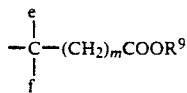

in which m is 0 to 3, and e and f when taken separately are, independently, hydrogen or $C_{1-3}$ alkyl, and when taken together with the carbon atom to which they are bonded form a 3 to 6-membered carbocyclic ring, and wherein $R^9$ is hydrogen, $C_{1-4}$ alkyl, or a carboxy-protecting ester-forming group.

A preferred value of $R^1$ when it is acylamino is of the formula

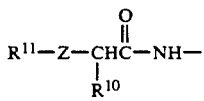

in which Z is oxygen or a direct bond and typical examples are those in which $R^{10}$ is hydrogen, amino or protected amino and $R^{11}$ is phenyl or substituted phenyl as defined above.

When $R^1$ in formula (I) is a diacylamino group, it can, for example, be a group of the formula

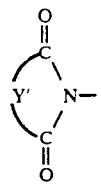

in which Y' is $C_{1-3}$ alkylene or o-phenylene. Examples of diacylamino groups represented by the above formula are phthalimido, succinimido, and maleimido.

When $R^1$ in formula (I) is a protected-amino group, $R^1$ is an amino group substituted by a conventional amino-protecting group used in the art for the temporary protection of an amino group. The protecting group can be of the formula

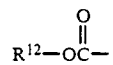

in which $R^{12}$ is $C_{1-6}$ alkyl, $C_{2-6}$ alkenyl, $C_{2-6}$ alkynyl, $C_{3-7}$ cycloalkyl, benzyl of substituted benzyl. Examples of such conventional protecting groups are the alkoxycarbonyl, substituted alkoxycarbonyl, cycloalkoxycarbonyl, bicylicalkoxycarbonyl, alkenyloxycarbonyl, and arylalkoxycarbonyl groups. Examples of these protecting groups are ethoxycarbonyl, cyclopentyloxycarbonyl, cyclohexyloxycarbonyl, 2,2,2-trichloroethoxycarbonyl, allyloxycarbonyl, 1-adamantyloxycarbonyl, t-butyloxycarbonyl, t-amyloxycarbonyl, benzyloxycarbonyl (Cbz), p-nitrobenzyloxycarbonyl, p-methoxybenzyloxycarbonyl, or diphenylmethoxycarbonyl. Other protecting groups are the trialkylsilyl-protecting groups such as trimethylsilyl, and the bis-trialkylsilyl-protecting groups such as N,N-bis-trimethylsilyl. Other convenient amino-protecting groups are the phthaloyl group and the formyl group. Such amino-protecting group serve as a blocking groups for the temporary protection of the amino group and subsequent to the process or even after further transformation of the 3-exomethylene product, can be removed and the product acylated to give the desired final product.

In the above formula (I), $R^2$ can be $C_{1-4}$ alkoxy, especially methoxy and ethoxy, and $C_{1-4}$ alkylthio, especially methylthio, ethylthio or n-butylthio. Preferably $R^2$ is hydrogen.

As defined above, $R^3$ can be an "ester-forming group". This term means any carboxylic acid esterforming group such as conventional carboxylic acid-protecting groups which can be removed by well known methods. Such groups are known in the art and it is preferred to select a group which is not readily reducible so that alteration of the group is avoided during the reaction. Examples include diphenylmethyl, benzhydryl, silyl, benzyl, p-methoxybenzyl, phenacyl, trimethylsilyloxy and tetrahydropyranyl. U.S. Pat. No. 4,052,387 describes additional examples of removable ester-forming groups.

The group $R^4$ is preferably hydrogen, and Z is most preferably iodo.

The process of the invention involves the use of a reagent comprising cobalt I. Such cobalt reagents are well known and comprise any compound or complex that provides cobalt in its I oxidation state. A preferred category of reagent is one in which the cobalt is complexed with appropriate ligands. Examples include cyano cobalt complexes, cobalt phthalocyanine, cobaloximes such as

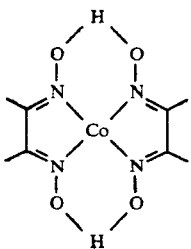

and vitamin $B_{12S}$, the latter being the most preferred. Other cobalt reagents suitable for use in the reaction are disclosed by R. Scheffold, Modern Synthetic Methods 1983, page 355 et seq.

Preferably the reagent is employed in an amount corresponding to from 1 to 1.4 equivalents per molecule of reactant of formula (II).

The reaction is performed under reducing conditions and preferably at least one equivalent, such as from 3 to 5 equivalents, of a reducing agent are employed per molecule of reactant. Suitable reducing agents include for example sodium borohydride and zinc.

Sodium borohydride is a preferred reducing agent and excess can be removed at the end of the reaction by addition of glacial acetic acid. Alternatively the reducing conditions can be provided electrochemically in which case the cathode acts as reducing agent.

Preferably the reaction is carried out in an aqueous organic solvent such as for example methanol, in which the reactant and reducing agent are soluble. A very convenient reaction system comprises aqueous methanol and sodium borohydride. In these conditions it is preferred to perform the reaction in an inert atmosphere such as for example nitrogen or argon and the reaction is preferably carried out at a temperature of from 10° C. to 30° C., such as ambient temperature.

Reactants of formula (II) of the following structure

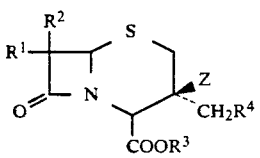
(III)

are either known compounds or can be synthesised by methods well known in the art. The preparation of compounds of this type is disclosed, for example, by T. Kamiya et al, Tetrahedron Letters, 1973, 3001, and by R. G. Micetich et al, Tetrahedron Letters, 1976, 979, and a convenient route to their preparation is summarised by the following reaction scheme

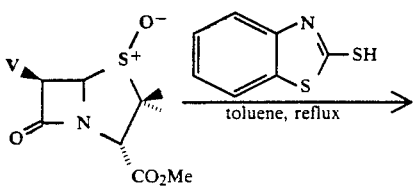

-continued

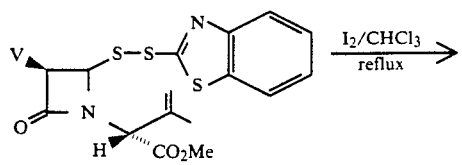

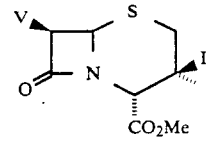

Yields of the desired exomethylene product are excellent when the reactant is of formula (III) above, and the preferred process of the invention is one in which Y takes the value

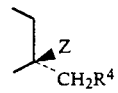

However the reaction also gives good yields with reactants of the formula

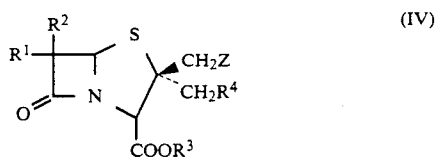
(IV)

Compounds of formula (IV) are either known or can be synthesised by methods well known in the art. For example such compounds are disclosed in R. G. Micetich et al, Tetrahedron Letters, 1976, 979.

The invention is illustrated by the following Examples

EXAMPLE 1

(1) Preparation of
$3\beta$-iodo-$3\alpha$-methyl-$7\beta$-phenoxyacetamidocepham-$4\alpha$-methylcarboxylate To a stirred solution of Kamiya's disulphide (derived from penicillin-V methyl ester sulphoxide (Tetrahedron Letters, 1973, 3001) [500 mg, 0.94 mmol] in chloroform (100 ml) was added iodine [120 mg, 1.0 eq] and the mixture refluxed for 24 hours under nitrogen. The solvent was removed in vacuo and the residue purified by column chromatography [flash silica gel 40 g, eluant; ethyl acetate-benzene, 1:1] affording the title compound [335 mg] as a colourless foam. TLC [ethylacetate-benzene 1:1]; Rf 0.6. Crystallised from ether-hexane, m.p. 118°-120° [lit., m.p. 118°-120°, cf Tetrahedron Letters 1976, 979] $\nu$max (CHCl$_3$); 1775, 1740, 1690, 1520 cm$^{-1}$ nmr, $\delta$H [300 MHz, CDCl$_3$] 2.22 (2H, s, Me), 2.98 (2H, ABq, J 15 Hz, C$\underline{H}_2$—S), 3.85(3H, s, COOMe), 4.70(2H, s, C$\underline{H}_2$OPh), 4.95(1H, s, C$\underline{H}$—CO$_2$Me), 5.42(1H, d, J 4 Hz, HN—C$\underline{H}$—CH—S), 5.83(1H, dd, J9 and 4H, HN—C$\underline{H}$—CH—S), 6.92-7.85(6H, m Ar$\underline{H}$ and N$\underline{H}$) ppm. m/z [EI]; 491(M+30), 300(80), 192(60), 168(100).

(2) Preparation of 3-exomethylene-7β-phenoxyacetamido cepham-4α-methylcarboxylate Brownish-blue coloured vitamin $B_{12s}$ [cobalt (I) species] was directly generated from the red coloured vitamin $B_{12}$ [290 mg 0.21 mmol] by treatment with sodium borohydride [18 mg, 3.0 eq.] in degassed methanol (15 ml) for 30 minutes at room temperature under argon. To the resulting brownish-blue solution was added 3β-iodo-7β-phenoxyacetamido cepham-4α-methyl carboxylate in degassed methanol (10 ml) and the mixture stirred for 30 minutes. To this solution was added glacial acetic acid (2 ml). Evaporation of the methanol and acetic acid was followed by partitioning between water (15 ml) and dichloromethane (10 ml×2). The organic layer was dried over anhydrous magnesium sulphate, filtered and the solvent was evaporated in vacuo, and then further dried under high vacuum to give the 3-exomethylene cepham [54.5 mg] TLC[diethyl ether]; Rf 0.5, m.p. 145°-147° C. (lit. 145°-147° C. Tetrahedron Letters, 1962, 3241). νmax[KBr]; 1765s (β-lactam), 1740s (ester) cm$^{-1}$ δH[300 MHz, CDCl$_3$]; 3.17, 3.68(2H, ABq, S—CH$_2$—C), 3.82(s, 3H, —COOMe), 4.68(s, 2H, —CH$_2$—OPh), 5.10(s, 1H, N—CH COOMe), 5.21(2H, d, J 6 Hz, —C=CH$_2$), 5.39(1H, d, J 4 Hz, HN—CH—CH—S), 5.69(1H, d, J4, 9 Hz, HN—CH—CH—S), 6.90-7.35 (m, 6H, NH and Ar-H) ppm δC[CDCl$_3$]; 29.369 t, —S—CH$_2$), 52.93 (q, COOCH$_3$) 56.36(d, HN—CH—CH—S), 58.67(d, HN—CH—CH—S), 67.23(t, CH$_2$OPh), 114.8, 122.3, 129.7 (d, 3×ArC), 117.24 (t, —C=CH$_2$), 133,5 (s, S—CH$_2$—C—CH$_2$), 157.0 (s, O—C Ar), 165.1, 168.2, 168.3 (3 ×s, 3×CO) ppm. m/z[DDI, NH$_3$] 380(100) 363(M+H)(35), 172(95).

EXAMPLE 2

(1) Preparation of 2β-iodomethyl-2α-methyl-7β-phenoxyacetamido penam-3α-methylcarboxylate To a solution of Kamiya's disulphide (derived from penicillin-V methyl ester sulphoxide (Tetrahedron Letters, 1973, 3001) [250 mg, 0.47 mmol] in dichloromethane (25 ml) was added iodine [83 mg, 1.4 eq] and the solution stirred overnight at room temperature. The solvent was removed in vacuo and the residue purified by column chromatography [flash silica gel 50 g, eluant, diethyl ether] to afford the iodopenam [168 mg] TLC[diethyl ether]; Rf 0.7 mp; 95°-98° C. νmax [CHCl$_3$]; 1785s (β-lactam), 1745s(ester), 1625s, 1500, 1250 cm$^{-1}$. δH[300 MHz, CDCl$_3$]; 1.65(3H, s, Me), 3.42 (2H, s, CH$_2$I), 3.82(3H, s, COOMe), 4.60(2H, ABq, CH$_2$—OPh), 5.01(1H, s, HN—CH—CH—S), 5.76 (1H, dd, J4, 9 Hz, HN—CH—CH—S), 6.95-7.38 (6H, m, ArH and NH) ppm m/z [DCI, NH$_3$], 491 (M+), (20), 168(100).

(2) Preparation of 3-exomethylene-7β-phenoxyacetamido cepham-4α-methylcarboxylate from 2β-iodomethyl-2α-methyl-7β-phenoxyacetamido penam-3α-methylcarboxylate.

To a stirred suspension of vitamin $B_{12}$ [262 mg, 0.19 mmol] in degassed methanol (20 ml) was added sodium borohydride [7.4 mg, 2.5 eq] and the mixture stirred for 30 minutes under argon. To this brown-blue solution was added the iodomethyl penam [95 mg, 0.19 mmol] in methanol (20 ml) and the mixture stirred for 20 minutes.

The reaction mixture was quenched by the addition of glacial acetic acid (3 ml) and the solvent removed in vacuo. The residue was partitioned between dichloromethane (20 ml) and water (20 ml) and the organic layer dried over anhydrous magnesium sulphate, filtered and evaporated. Purification by column chromatography [flash silica gel 25 g, eluant; diethyl ether] gave the 3-exomethylene cepham as a solid [21 mg].

TLC[diethyl ether]; Rf 0.5, m.p. 145°-147° C. νmax[KBr]; 1765s (β-lactam), 1740s (ester) cm$^{-1}$ δH[300 MHz, CDCl$_3$]; 3.17, 3.68 (2H, ABq, S—CH$_2$—C), 3.82 (s, 3H, —COOMe), 4.68 (s. 2H—CH$_2$—OPh), 5.10 (s. 1HN—CH—COOMe, 5.20, 5.21 (2×1H, 2×s, C=CH$_2$), 5.39 (1H, d, J4Hz, HN—CH—CH—S), 5.69 (1H, d, J4.9 Hz, HN—CH—CH—S), 6.90-7.35 (m, 6H, NH and Ar-H) ppm.

δC[CDCl$_3$]; 29.36 (t, —S—CH$_2$), 52.93 (q, COOCH$_3$), 56.36 (d, HN—CH—CH—S), 58.67 (d, HN—CH—CH—S), 67.23 (t, —CH$_2$OPh), 114.8, 122.3, 129.7 (d, 3×ArC), 117.24 (t, —C=CH$_2$), 133.5 (s, S—CH$_2$—C=CH$_2$), 157.0 (s, O—C Ar), 165.1, 168.2, 168.3 (3×s, 3×CO) ppm.

m/z [DCI, NH$_3$]; 347 (MH+, 80), 289 (48), 172 (100).

I claim:

1. A process for preparing a compound of the formula

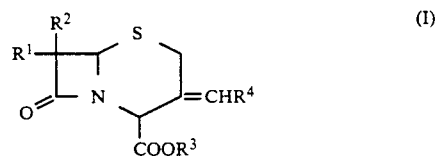

in which
R$^1$ is an amino group, a protected amino group, an acylamino group or a diacylamino group,
R$^2$ is hydrogen, C$_{1-4}$ alkoxy or C$_{1-4}$ alkylthio,
R$^3$ is hydrogen, a salt ion or an ester-forming group, and
R$^4$ is hydrogen or C$_{1-3}$ alkyl, which comprises reacting a compound of the formula

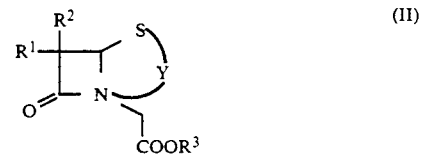

in which Y is a bridging group of the formula

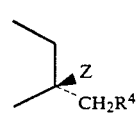

or

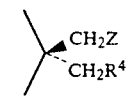

Z is chloro, bromo or iodo, and R$^1$, R$^2$, R$^3$ and R$^4$ have the above defined values, with a reagent providing cobalt I, under reducing conditions.

2. A process according to claim 1 for preparing a compound in which Y is

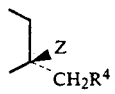

and Z and R⁴ have the values defined in claim 1.

3. A process according to claim 1, in which R⁴ is hydrogen and Z is iodo.

4. A process according to claim 1, in which R² is hydrogen.

5. A process according to claim 1, in which R¹ is

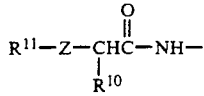

in which Z is oxygen or a direct bond, $R^{10}$ is hydrogen, amino or protected amino and $R^{11}$ is phenyl or substituted phenyl.

6. A process according to claim 5, in which $R^{11}$ is phenyl, Z is oxygen, and $R^{10}$ is hydrogen.

7. The process of claim 5 wherein the cobalt I reagent is vitamin $B_{12}$.

8. The process of claim 5 wherein the reducing agent is sodium borohydride.

* * * * *